United States Patent [19]
Wagner

[11] Patent Number: 6,128,123
[45] Date of Patent: Oct. 3, 2000

[54] WAVELENGTH-TUNABLE EYE PROTECTION

[75] Inventor: Harvey Lawrence Wagner, Royersford, Pa.

[73] Assignee: Lockheed Martin Corp., Sunnyvale, Calif.

[21] Appl. No.: 08/407,145

[22] Filed: Mar. 20, 1995

[51] Int. Cl.[7] .................................................. G02B 26/00
[52] U.S. Cl. ...................... 359/260; 359/614; 359/578; 359/579; 359/885; 351/44
[58] Field of Search .............................. 351/44; 359/614, 359/578, 579, 885, 260

[56] References Cited

U.S. PATENT DOCUMENTS

| | | | |
|---|---|---|---|
| 3,699,347 | 10/1972 | Buchan et al. ...................... | 250/213 R |
| 4,202,601 | 5/1980 | Burbo et al. ............................... | 351/49 |
| 4,508,964 | 4/1985 | Gunning, III et al. .................. | 250/201 |
| 5,132,826 | 7/1992 | Johnson et al. ............................ | 359/93 |

*Primary Examiner*—Georgia Epps
*Attorney, Agent, or Firm*—W. H. Meise

[57] ABSTRACT

An eye protection arrangement for protection against multispectral laser threats includes goggles or spectacles with a tunable etalon optical filter. In one embodiment, the optical filter is fixed-tuned to a safe frequency. In another embodiment, light from the laser being used is sensed, and used to set the protective goggles to a different wavelength than the laser. In yet another embodiment of the invention, the protective optical filters have a comb response, and additional protection is provided by optically cascading two filters, each having a somewhat different comb response, so as to reduce the number of transmission spectra.

7 Claims, 4 Drawing Sheets

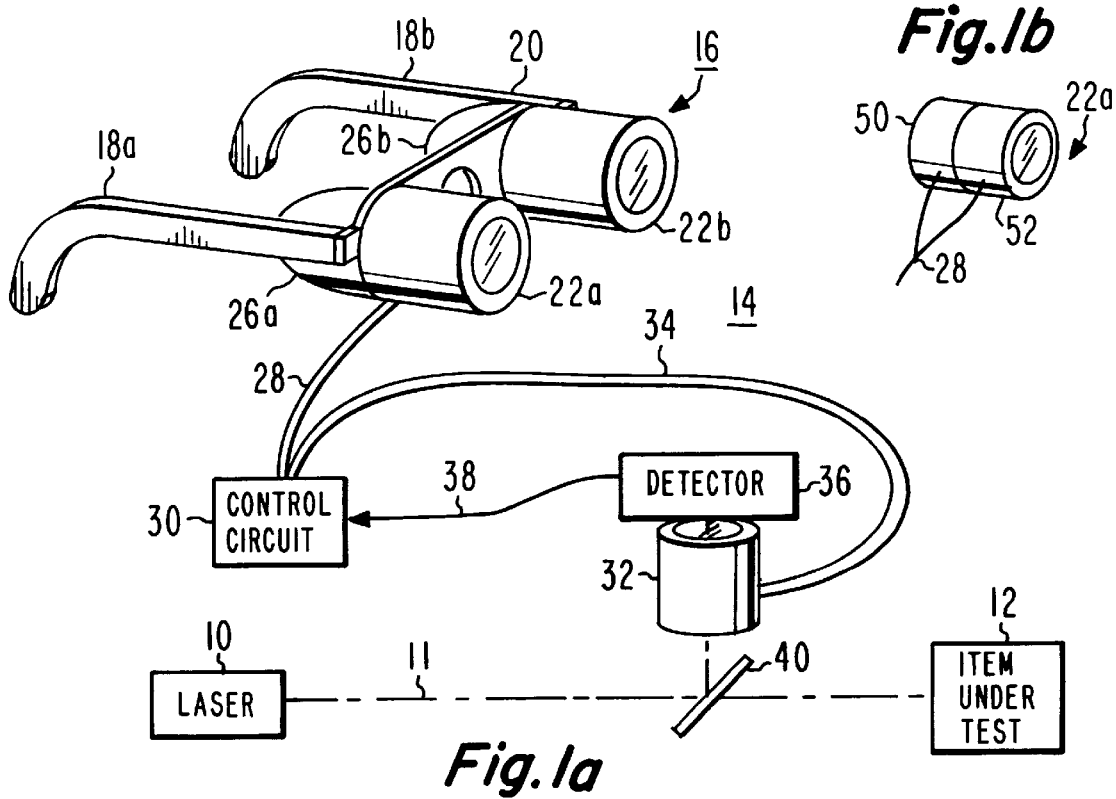
Fig.1b
Fig.1a
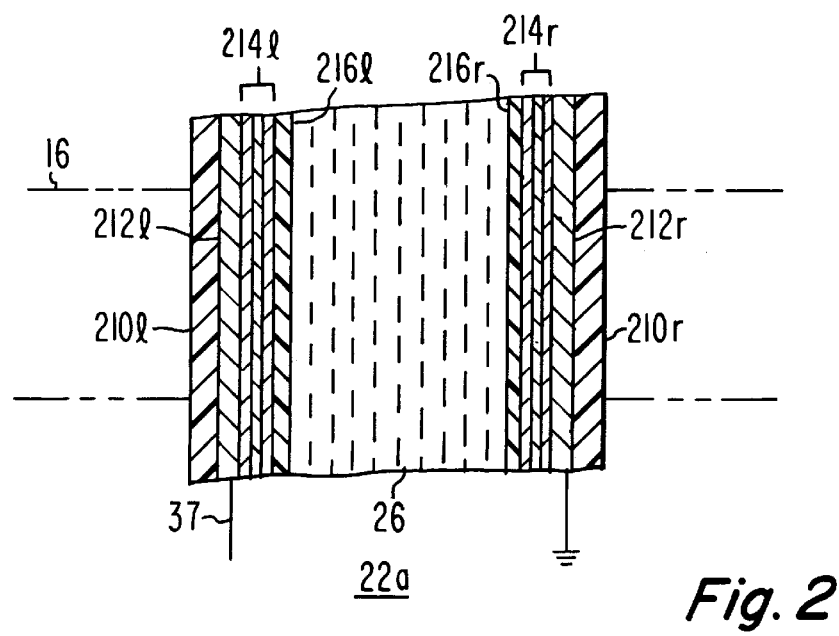
Fig. 2

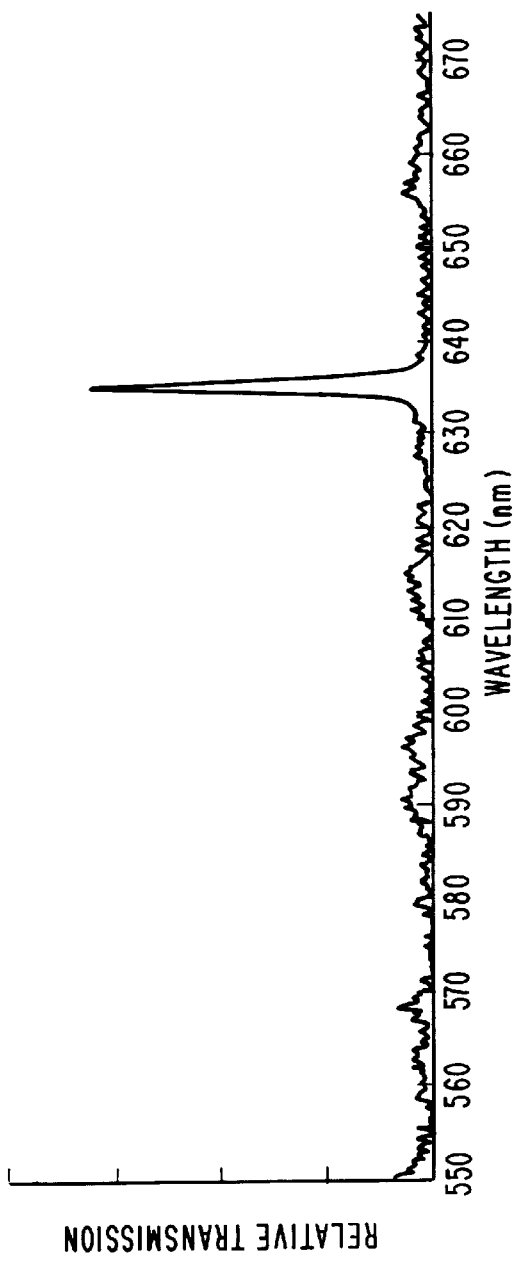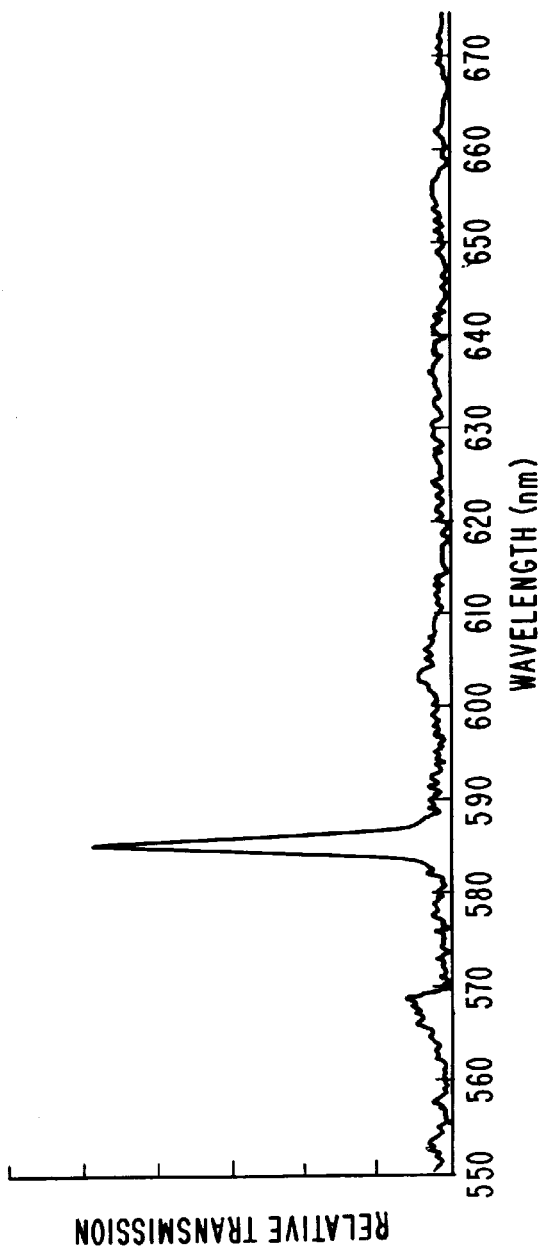

WAVELENGTH-TUNABLE EYE PROTECTION

The Government has rights in this invention pursuant to contract no. F33615-92-C5927 with the Department of the Air Force.

FIELD OF THE INVENTION

This invention relates to eyewear for eye protection against strong lights, such as lasers, and more particularly to such eyewear which includes tunable etalons.

BACKGROUND OF THE INVENTION

Lasers are becoming more common in industrial, communications, and military applications. A laser generates a beam of collimated light, which tends to remain in a tight beam over long distances. Many lasers produce sufficient total power to damage eyes from distances of a thousand feet or more. Even relatively low-power lasers, which might be used, for example, for driving fiber-optic cables in a communication system, produce sufficient power density so that, if inadvertently directed in to an eye, damage may occur. Consequently, a need exists for eyeware for protection against eye damage when working around lasers. In the past, most lasers were fixed-wavelength, and suitable eyeware might consist of a notch filter at the known wavelength of the laser being used. With the advent of systems using tunable lasers or multiple lasers, and with the possibility of lasers being intentionally used in military situations to cause eye damage, the eye protection problem is exacerbated. It is not practical to provide a distinct optical filter which covers all possible optical wavelengths in a tunable laser or multispectral laser threat environment, because such an eye protector would not pass any light, thereby protecting the eyes of the user by rendering him sightless for the duration of the period of the protection. Improved eye protection is desired.

SUMMARY OF THE INVENTION

An eye protection arrangement for protection against multispectral laser threats includes goggles or spectacles with a tunable etalon optical filter. In one embodiment, the optical filter is fixed-tuned to a safe frequency. In another embodiment, light from the laser being used is sensed, and used to set the protective goggles to a different wavelength than the laser. In yet another embodiment of the invention, the protective optical filters have a comb response, and additional protection is provided by optically cascading two filters, each having a somewhat different comb response, so as to reduce the number of transmission spectra.

An eye protection device according to the invention includes a wavelength-tunable filter for passing at least one wavelength selected in response to a control signal. A mounting arrangement is provided for mounting the filter before at least one eye of a user. A controller is coupled to the filter for setting the passing wavelength of the filter to a wavelength other than a wavelength at which a high-power-density light source emits. In a particular embodiment of the invention, the controller produces a signal which is constant, and which may be selected by the user. In another embodiment, the controller includes a second light filter with characteristics similar to or preferably identical to those of the filter located before the eye, and a light detector coupled to the output of the second filter. The controller also includes logic for adjusting the control signal so that both the first-mentioned and the second filters attenuate the light from the source more than adjoining wavelengths.

The light filter, in a preferred embodiment of the invention, is a comb filter.

In one embodiment, the filter is a tunable Fabry-Perot etalon. The tuning may be provided by liquid crystal material within the etalon cavity. In another embodiment of the invention, at least one of the filters is a cascade of two Fabry-Perot etalons, either dimensioned or controlled to have somewhat different transmission comb spectra.

DESCRIPTION OF THE DRAWING

FIG. 1a is a representation of an optical protective device in accordance with a first embodiment of the invention, having at least a portion of a controller therefor associated with a laser source, and FIG. 1b is a simplified representation of an optically cascaded filter according to another aspect of the invention;

FIG. 2 is a simplified cross-sectional view of a tunable Fabry-Perot etalon filter in accordance with an aspect of the invention;

FIG. 4a and 4b are wavelength responses of an optical cascade of two tunable optical filters;

DESCRIPTION OF THE INVENTION

Figure 3:
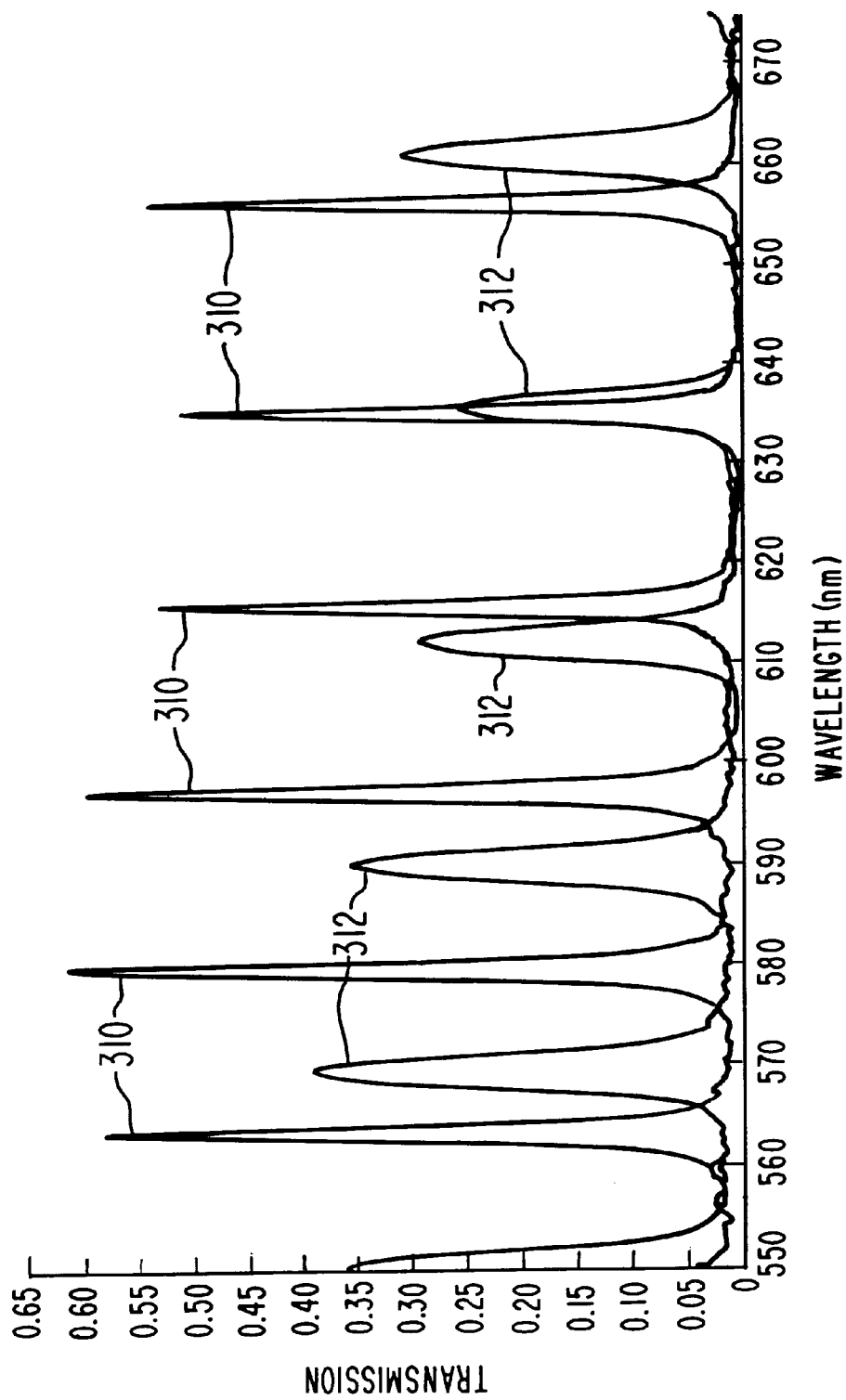
FIG. 3 plots comb filter wavelength responses of structures such as that of FIG. 2 and cascades thereof.

FIG. 1a is a simplified representation of a laser 10 generating a light beam 11, which is directed toward an item under test, represented by a block 12. The person operating the laser system is protected from inadvertent exposure of the eyes by a system designated generally as 14, which includes protective spectacles or goggles 16. Spectacles 16 include right and left earpieces 18a and 18b, respectively, and a bridge 20. Bridge 20 supports right and left controlled optical filters 22a and 22b, respectively. Right and left side shields 26a and 26b protect the eyes of the wearer from laser light impinging from the sides.

Controllable filters 22a and 22b of FIG. 1a are controlled by signals applied over a signal path 28 from a control circuit 30. A half-silvered light splitter 40 splits off a portion of light beam 11, and directs it toward a further controllable filter 32, which preferably identical to controllable filters 22a and 22b. Controllable filter 32 is controlled by way of a signal path 34 from controller 30, and filters the light in the same manner as either of filters 22a or 22b. The filtered light from filter 32 is applied to a light detector 36, for generating an electrical signal in response to the received light. The electrical signal from detector 36 is applied to control circuit 30, to provide it with the sensed signal required for control operation.

In FIG. 1a, controllable filters 22a, 22b, and 32 are wavelength-tunable Fabry-Perot transmission-type etalons. Such etalons are described, for example, in U.S. Patent application Ser. No. 08/234,771, filed Apr. 28, 1994 in the name of Wagner. FIG. 2 is a more detailed diagram of a filter of FIG. 1a. For definiteness, filter 22a is represented. In FIG. 2, filter 22a is a tunable liquid-crystal Fabry-Perot etalon, also known generally as a Fabry-Perot interferometer, tunable etalon, resonant cavity interferometer, and the like. Filter 22a of FIG. 2 includes transparent silica or quartz left and right substrates 210l and 210r, respectively, which preferably have mutually parallel interior surfaces. The inside surfaces of substrates 210*l* and 210*r* are each coated with a layer 212*l*, 212*r*, respectively, of transparent electrical conductor material, which may be, for example, tin oxide or indium-tin oxide. Conductive layer 212*r* is connected to ground, and conductive layer 212*l* is connected to conductor 37 for receiving voltages which are selected by controller 30, as described above in conjunction with FIG. 1*a*. A partially transparent or semitransparent reflector 214*l* overlies electrically conductive layer 212*l*, and a similar semitransparent reflector 214*r* overlies conductor 212*r*. Such a semitransparent reflector layer corresponds conceptually to a "half-silvered" or "one-way" mirror, but such half-silvered mirrors tend to have high attenuation or loss. Instead, semitransparent reflector layers 214*l* and 214*r* are layered dielectrics, known in the art for low loss, selected to produce the desired semi-transparency and reflectivity. A cavity 26 lying between semitransparent reflectors 214*l* and 214*r* is filled with liquid crystal material. A further pair of layers 216*l* and 216*r* of buffed polyimide may be placed on reflector layers 214*l* and 214*r*, respectively, for aiding in aligning the molecules of the liquid crystal.

The liquid crystal material filling cavity 26 of the etalon of FIG. 2 exhibits birefringence, which is a difference in the index of refraction, depending upon the polarization of the light which passes therethrough relative to the orientation of the liquid crystals. This may be explained by noting that under normal, unenergized conditions, the liquid crystal material in cavity 26 tends to assume a "crystalline" form, with the molecules aligned in a particular direction, illustrated in FIG. 2 as being the vertical direction. The direction of the preferred orientation may be controlled by forming mutually parallel grooves in the polyimide interior surfaces facing the cavity, which orient the molecules adjacent the surface parallel to the grooves, and thereby establish the "crystal" orientation. Under the condition of vertical molecular alignment, light which is principally polarized vertically will experience a particular propagation delay, which relates to the index of refraction. When a voltage is applied by way of conductor 37 to generate an electric field across the liquid crystal material in cavity 26, the molecules of the liquid crystal material tend to rotate approximately 90° to become parallel with the field, whereupon they are no longer parallel to the electric field component of the incident light, and the propagation delay, and consequently the index of refraction, changes. The change in delay corresponds to changing the effective length of cavity 20 as a function of the applied voltage. Whatever the actual mechanism by which the result is accomplished, an etalon such as that described in conjunction with FIG. 2 has the property of filtering light at frequencies which depend upon the applied voltage. Some embodiments of an etalon filter may exhibit preferred axes of polarization, i.e. the performance is best for a particular polarization of light passing therethrough. A polarizing filter (not illustrated) may be inserted into the light path for best performance.

As known to those skilled in the art, Fabry-Perot etalons typically have a periodic filter function given by $$2nd\cos\theta = m\lambda \quad (1)$$

where
  n is the refractive index of the medium;
  d is the mirror spacing;
  θ is the inclination of the normal of the mirrors;
  m is the order of the interference; and
  λ is the wavelength.

For the case of mutually parallel mirrors, cos θ is unity. In general, the etalon passes or transmits light at a wavelength at which the cavity length is a multiple of fractional submultiples of a wavelength. This may be understood by considering that, in order to transmit light, the multiple internal reflections must constructively add at the output semitransparent layer, and that an even number of reflections must occur for light to exit. The comb or multispectral response of one of the etalons, such as etalon 20 of FIG. 1*a*, is illustrated by plot 310 of FIG. 3. As illustrated, the transmission peaks occur periodically at wavelengths of 564, 580, 597, 616, 635, and 655 nm.

If the wavelength of the laser 10 of FIG. 1*a* is at a fixed frequency, then a tunable spectacle or goggle in accordance with the invention is not necessary, but it can be used in that case, too. If the laser source has fixed wavelength, the control circuit 30 does not even need an input from detector 36, but instead control circuit 36 needs only to produce an alternating voltage of a magnitude selected to place the peaks of the transmission spectrum of the etalons 22*a*, 22*b* at a wavelength other than the wavelength of the laser. Since the laser frequency is fixed in this particular arrangement, no tuning is required. With the transmission peaks of the filters 22*a* and 22*b* at wavelengths other than the laser wavelength, the laser wavelength is at a null in the transmission response. Thus, light from laser 10 of FIG. 1 cannot pass through the spectacles, or, more properly, the light is attenuated.

If, on the other hand, laser 10 of FIG. 1*a* is tunable, the wavelength may at some time reach one of the spectral transmission peaks of plot 310, at which time the goggles would not provide protection of the user's eyes against an inadvertent reflection of the laser light. In accordance with the invention, control circuit 30 adjusts the control signal on signal paths 28 and 34 so as to reset the peaks of the transmission wavelength spectrum of the light filters away from the transmission wavelength of laser 10.

It should be noted that the case of a fixed laser frequency or wavelength, the voltage required to tune the filter depends upon the angle of incidence of the light on the filter. A fixed tuning voltage is applicable only to normal incidence, which will seldom be the case. Thus, even for a fixed-tuned laser, it is desirable to have a tunable wavelength filter in the spectacles.

For some applications, such as protection of military personnel from intentional laser exposure, it may be advantageous to reduce the number of transmission peaks in the transmission spectrum of each of the protective filters 22*a*, 22*b*. For this purpose, each of filters 22*a*, 22*b* may be made as a cascade of two slightly different etalon filters. For example, filter 22*a* may be made as a cascade of two etalon filters, one of which has a wavelength spectrum as illustrated in plot 310 of FIG. 3. FIG. 1*b* illustrates a filter, such as filter 22*a* of FIG. 1*a*, made up as an optical cascade of two separate tunable filters 50 and 52. The first filter 50 of the arrangement of FIG. 1*b* may have a response similar to that of plot 310 of FIG. 3, and the second filter 52 may have a wavelength spectrum which is illustrated as plot 312 of FIG. 3.

According to an aspect of the invention, filter 22*a* of FIG. 1*b*, is an optical cascade of two structures such as that of FIG. 2. This optical cascade is similar in construction to two filters 22 illustrated in FIG. 2, each with slightly different characteristics, to produce a comb spectrum different from comb spectrum 310 of FIG. 3. This is most readily accomplished by making the width of cavity 26 of FIG. 2 of the two optically cascaded filters of different dimensions, which changes the "order number" m of equation (1), which, together with other parameters, determines the filter transmission spectrum. Plot 312 of FIG. 3 represents the transmission spectrum of a filter with different characteristics than the filter having plot 310. As illustrated, plot 312 has transmission peaks at about 551, 569, 590, 612, 635, and 661 nm. None of these transmission peaks, except the peak at about 635 nm, corresponds with a transmission peak of plot 310. Consequently, the only spectral line or band which is transmitted by both filters is the one which peaks at about 635 nm, and one or the other of the two optically cascaded filters attenuates or rejects all other wavelengths. Thus, the optical cascade of two filters used as filter 22a of FIG. 1a, when set to voltages giving the spectral responses illustrated in FIG. 3, passes only 635 nm, corresponding to a red hue. A green hue at about 550 nm could be transmitted by the pair of filters, by leaving filter 22 of FIG. 1a with the response illustrated as 312 in FIG. 3, and by modifying response 310 of filter 20 to move the set of peaks of plot 310 to the left, toward smaller wavelengths, until the peak illustrated at 562 nm overlies the peak at 550 nm. Blue at about 480 nm is not illustrated in FIG. 3, but the same principles apply to blue. While retuning of a single filter may provide filtering, optimum response may require retuning of both filters by the control circuit 30 of FIG. 1a. FIGS. 4a and 4b are plots of the spectral response of a pair of optically cascaded filters, with both filters retuned for optimum combined response. In FIG. 4a, the combined transmission response is at 634 nm, and in FIG. 4b, the combined transmission response is at 585 nm. Those skilled in the art know that the bandwidth of the etalon filter transmission peaks may be controlled by, for example, controlling the amount of transmission provided by partially-reflective surfaces 214 of FIG. 2. The bandwidth is selected in accordance with the severity of the threat. In a laboratory in which several tunable lasers are in use, the two-cascaded-filter arrangement may provide more protection.

Figure 5:
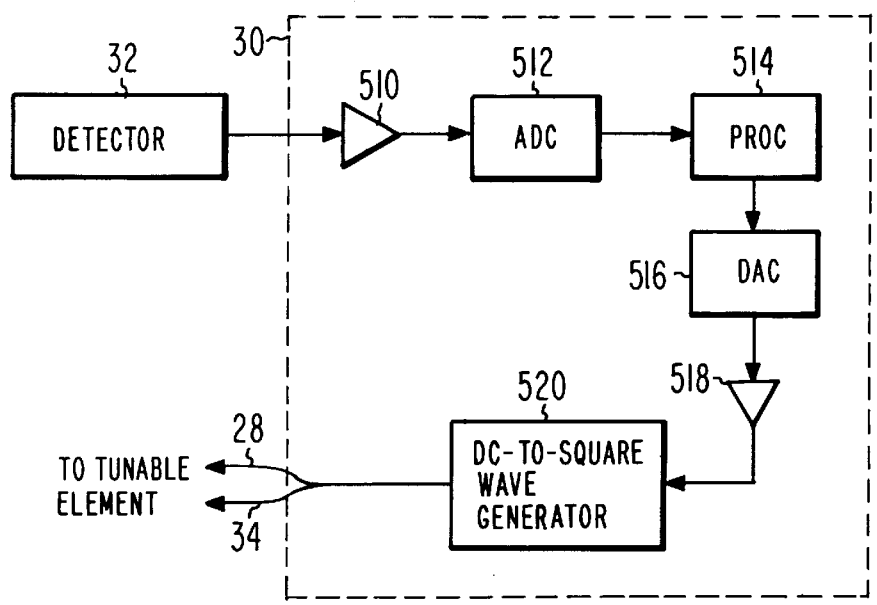
FIG. 5 is a simplified block diagram of a control circuit which may be used in the arrangement of FIG. 1.

FIG. 5 is a simplified block diagram illustrating details of the control circuit for the spectacles of FIG. 1. In FIG. 5, light detected by detector 32 produces signals which are coupled to control circuit 30. Control circuit 30 includes an amplifier 510, which amplifies the signals, and applies them to an analog-to-digital converter (ADC) 512. ADC 512 converts the analog signals to digital form. The digital signals from ADC 512 are applied to a processor 514, which processes the signals as described in more detail below. The processed signals from processor 514 are filter element tuning voltage signals in digital form. The filter element tuning voltage signals are applied to a digital-to-analog converter (DAC) 516, which produces analog signals which represent the amplitude of the tuning voltages. The analog signals from DAC 516 are applied by way of a driver amplifier 518 to a DC-to-AC converter 520. Converter 520 "chops" or converts the unipolar signal from driver amplifier 518 into an alternating or square-wave signal with related peak amplitude. The alternating voltage from converter 520 is applied to the liquid-crystal etalon tuning elements 22a and 32 by way of signal paths 28 and 34, respectively. The etalon filter elements are assumed to be identical for purposes of this control system, so the etalon filter associated with the spectacles tunes to block the same wavelength that is blocked by filter 32, and the eyes are protected against the particular laser wavelength.

Figure 6:
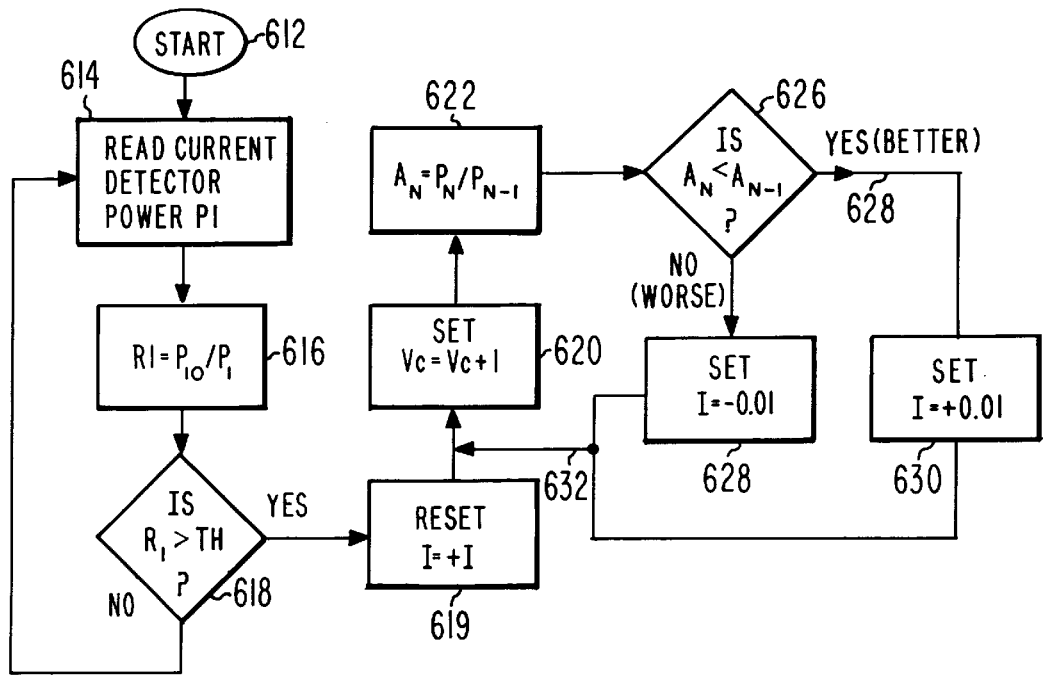
FIG. 6 is a simplified flow chart illustrating details of the operation of the control circuit of FIG. 5.

FIG. 6 is a simplified flow chart illustrating a control scheme for controlling spectacles 16. In FIG. 6, the logic starts at a START block 612, and proceeds to a block 614, which represents the reading of the current detector signal power or amplitude P1.

From block 614, the logic flows to a block 616, which represents comparison of the current amplitude P1 with the amplitude a few clock cycles previously, which may be ten clock cycles, for example. Thus, block 616 represents taking the ratio $R1=P_{10}/P_1$. A sudden rise in the ratio R1 thus gives an indication of whether a laser has directed a beam into the spectacles. The logic proceeds to a decision block 618, which compares ratio $R_1$ with a threshold TH, chosen to indicate the presence of a threat to the eyes. If the current value of $R_1$ is less than threshold TH, the logic flows back to block 614. As so far described, the logic of blocks 614, 616, and 618 represents the main logic loop, which monitors the incident power for sudden increases in the light power entering the detector.

In the event of a sudden rise in the ratio $R_1$, indicative of the appearance of a threat to the eyes, the logic leaves decision block 618 of FIG. 6 by the YES path, and arrives at a block 619, which represents the setting of a variable I to its positive value +I. From block 619, the logic flows to a block 620, which represents the incrementing of the current value of the tuning voltage Vc to a new value of Vc+I, where I is a small increment value, such as +0.01. From block 620, the logic flows to a further block 622, which represents measuring the amplitude ratio $A_N=(P_N/P_{N-1})$ between one clock cycle and the next, to aid in indicating control direction. From block 622, the logic flows to a decision block 626, which compares the current value of $A_N$ with $A_{N-1}$, to see if the detected power has increased or decreased as a result of the slight tuning change. If $A_N$ is less than $A_{N-1}$, the logic leaves decision block 626 by the YES output, which indicates that the power transmitted through filter 32 to detector 36 has decreased. The YES output of decision block 626 directs the logic by a path 628 to a block 630, which represents setting the current value of I to +I, to continue the same direction of control. From block 630, the logic then flows by a path 632 back to block 620, where the current value of I is added to control voltage Vc. Since I has a positive value, the logic again increments the value of Vc. The logic proceeds about the loop including blocks 620, 622, 626, and 630 until such time as the detected power no longer decreases. At this time, decision block 626 directs the logic by its NO output to a block 628, which represents resetting of the current value of I to –I. From block 628, the logic flows back to block 620, where the value –I is added to Vc, thereby decreasing Vc. The logic then flows around the loop, alternating between the paths including blocks 628 and 630. Such loops are well known in the art, and may be configured to take into account various contingencies. The logic flow of FIG. 6 in essence detects the presence of a laser threat by a rapid rise of detected power, and then generates a digital ramp voltage which progressively detunes the filter, to thereby progressively reject the increased power, until the amount of attenuation reaches a maximum, following which the filter dithers about the maximum-attenuation point.

Other embodiments of the invention will be apparent to those skilled in the art. For example, the control circuit may employ analog circuitry instead of, or together with, digital circuitry. While ten clock cycles "delay" are described as having been used in the logic of FIG. 6 between successive sensing times, the number of clock cycles will depend upon system time constants and upon the processor clock rate, and may be greater or fewer.

What is claimed is:

1. An eye protection device for protection against light from a source of light, said device comprising:

a wavelength-tunable filter for passing at least one wavelength selected in response to a control signal;

mounting means for mounting said filter before at least one eye of a user; and control means coupled to said filter for setting said passing wavelength to a wavelength other than a wavelength at which said light source emits.

2. A device according to claim 1, wherein said filter comprises a wavelength-tunable etalon.

3. A device according to claim 1, wherein said control means comprises means for generating light filter control signals, and for coupling said light control signals to said wavelength-tunable filter, for controlling said filter to reduce the amplitude of light passing therethrough at said wavelength at which said light source emits.

4. An eye protection device comprising a first wavelength-tunable filter for passing at least one wavelength selected in response to a control signal;

mounting means for mounting said first filter before at least one eye of a user; and control means coupled to said first filter for generating said control signal for setting said passing wavelength to a wavelength other than a wavelength at which a light source emits, wherein said control means comprises:

a second wavelength-tunable filter for passing said at least one wavelength which is passed by said first wavelength-tunable filter;

means for coupling light from said light source to said second wavelength-tunable filter, for generating second light signals at the output of said second wavelength-tunable filter, which second light signals correspond to those which are passed by said first wavelength-tunable filter; and light detection and processing means coupled to said first and second wavelength-tunable filters, for detecting said second light signals, and for generating light filter control signals, and for coupling said light control signals to said first and second wavelength-tunable filters, for controlling said filters to reduce the amplitude of light passing therethrough at said wavelength at which a light source emits.

5. A device according to claim 1, wherein said filter comprises comb filtering means.

6. A device according to claim 5, wherein said comb filtering means comprises a Fabry-Perot etalon.

7. A device according to claim 5, wherein said comb filtering means comprises cascaded Fabry-Perot etalons.

* * * * *